United States Patent
Meyer et al.

(10) Patent No.: US 6,953,755 B2
(45) Date of Patent: Oct. 11, 2005

(54) TECHNIQUE FOR MONITORING THE STATE OF METAL LINES IN MICROSTRUCTURES

(75) Inventors: Moritz Andreas Meyer, Dresden (DE); Ehrenfried Zschech, Moritzburg (DE); Eckhard Langer, Radebeul (DE)

(73) Assignee: Advanced Micro Devices, Inc., Austin, TX (US)

( * ) Notice: Subject to any disclaimer, the term of this patent is extended or adjusted under 35 U.S.C. 154(b) by 54 days.

(21) Appl. No.: 10/677,911

(22) Filed: Oct. 2, 2003

(65) Prior Publication Data

US 2005/0072919 A1 Apr. 7, 2005

(30) Foreign Application Priority Data

Oct. 2, 2003 (DE) .......................... 103 46 026

(51) Int. Cl.[7] .......................... G01R 31/28; H01L 21/44
(52) U.S. Cl. ...................... 438/795; 438/799; 438/660; 438/14; 250/306; 250/307; 250/310
(58) Field of Search ................ 250/306, 307, 250/310; 438/14, 660, 799, 795

(56) References Cited

U.S. PATENT DOCUMENTS 5,124,645 A  6/1992  Rhoden et al. .......... 324/158 F
5,930,587 A * 7/1999  Ryan ........................... 438/14
2004/0239318 A1 * 12/2004 Xiao et al. ................. 324/244

OTHER PUBLICATIONS

Lau et al., "In situ electron microscopy studies of electromigration in stacked Al(Cu)/Tin interconnects," *Applied Physics Letters*, 76:164–66, 2000.

Meyer et al., In situ SEM observation of electromigration phenomena in fully embedded copper interconnect structures, *Microelectronic Engineering*, 64:375–82, 2002.

Schneider et al., "Electromigration in passivated Cu Interconnects studied by transmission x-ray microscopy," *J. Vac. Sci. Technol.*, 20:3089–94, 2002.

Xu et al., "Quantitative metrology study of Cu/SiO$_2$ interconnect structures using fluorescence x-ray microscopy," *Applied Physics Letters*, 78:820–22, 2001.

* cited by examiner

*Primary Examiner*—Nikita Wells
(74) *Attorney, Agent, or Firm*—Williams, Morgan & Amerson, P.C.

(57) ABSTRACT

By preparing fully-embedded interconnect structure samples for a cross-section analysis by means of electron microscopy or x-ray microscopy, degradation mechanisms may be efficiently monitored. Moreover, displaying some of the measurement results as a quick motion representation enables the detection of subtle changes of characteristics of an interconnect structure in a highly efficient manner.

47 Claims, 4 Drawing Sheets

TECHNIQUE FOR MONITORING THE STATE OF METAL LINES IN MICROSTRUCTURES

BACKGROUND OF THE INVENTION

1. Field of the Invention

Generally, the present invention relates to the formation of microstructures, such as advanced integrated circuits, and, more particularly, to the formation and examination of conductive structures, such as metal regions, and their characteristics during stress conditions.

2. Description of the Related Art

In the fabrication of modern microstructures, such as integrated circuits, there is a continuous drive to steadily reduce the feature sizes of microstructure elements, thereby enhancing the functionality of these structures. For instance, in modern integrated circuits, minimum feature sizes, such as the channel length of field effect transistors, have reached the deep sub-micron range, thereby increasing performance of these circuits in terms of speed and/or power consumption. As the size of individual circuit elements is reduced with every new circuit generation, thereby improving, for example, the switching speed of the transistor elements, the available floor space for interconnect lines electrically connecting the individual circuit elements is also decreased. Consequently, the dimensions of these interconnect lines have to be reduced to compensate for a reduced amount of available floor space and for an increased number of circuit elements provided per unit die area. The reduced cross-sectional area of the interconnect lines, possibly in combination with an increase of the static power consumption of extremely scaled transistor elements, may require a plurality of stacked metallization layers to meet the requirements in view of a tolerable current density in the metal lines.

Advanced integrated circuits, including transistor elements having a critical dimension of 0.13 $\mu$m and even less, may, however, require significantly increased current densities in the individual interconnect lines despite the provision of a relatively large number of metallization layers owing to the significant number of circuit elements per unit area. Operating the interconnect lines at elevated current densities, however, may entail a plurality of problems related to stress-induced line degradation, which may finally lead to a premature failure of the integrated circuit. One prominent phenomenon in this respect is the current-induced material transportation in metal lines, also referred to as "electromigration," which may lead to the formation of voids within and hillocks next to the metal line, thereby resulting in reduced performance and reliability or complete failure of the device. For instance, aluminum lines embedded into silicon dioxide and/or silicon nitride are frequently used as metal for metallization layers, wherein, as explained above, advanced integrated circuits having critical dimensions of 0.18 $\mu$m or less, may require significantly reduced cross-sectional areas of the metal lines and, thus, increased current densities, which may render aluminum less attractive for the formation of metallization layers.

Consequently, aluminum is increasingly being replaced by copper that exhibits a significantly lower resistivity and exhibits significant electromigration effects at considerably higher current densities as compared to aluminum. The introduction of copper into the fabrication of microstructures and integrated circuits comes along with a plurality of severe problems residing in copper's characteristic to readily diffuse in silicon dioxide and a plurality of low-k dielectric materials. To provide the necessary adhesion and to avoid the undesired diffusion of copper atoms into sensitive device regions, it is, therefore, usually necessary to provide a barrier layer between the copper and the dielectric material in which the copper lines are embedded. Although silicon nitride is a dielectric material that effectively prevents the diffusion of copper atoms, selecting silicon nitride as an interlayer dielectric material is less then desirable, since silicon nitride exhibits a moderately high permittivity, thereby increasing the parasitic capacitances of neighboring copper lines. Hence, a thin conductive barrier layer that also imparts the required mechanical stability to the copper is formed so as to separate the bulk copper from the surrounding dielectric material and only a thin silicon nitride or silicon carbide or silicon carbonitride layer in the form of a capping layer is frequently used in copper-based metallization layers. Currently, tantalum, titanium, tungsten and their compounds, with nitrogen and silicon and the like, are preferred candidates for a conductive barrier layer, wherein the barrier layer may comprise two or more sub-layers of different composition so as to meet the requirements in terms of diffusion suppressing and adhesion properties.

Another characteristic of copper significantly distinguishing it from aluminum is the fact that copper may not readily be deposited in larger amounts by chemical and physical vapor deposition techniques, in addition to the fact that copper may not be efficiently patterned by anisotropic dry etch processes, thereby requiring a process strategy that is commonly referred to as the damascene or inlaid technique. In the damascene process, first a dielectric layer is formed, which is then patterned to include trenches and vias which are subsequently filled with copper, wherein, as previously noted, prior to filling in the copper, a conductive barrier layer is formed on sidewalls of the trenches and vias. The deposition of the bulk copper material into the trenches and vias is usually accomplished by wet chemical deposition processes, such as electroplating and electroless plating, thereby requiring the reliable filling of vias with an aspect ratio of 5 and more with a diameter of 0.3 $\mu$m or even less in combination with trenches having a width ranging from 0.1 $\mu$m to several $\mu$m. Although electrochemical deposition processes for copper are well established in the field of electronic circuit board fabrication, a substantially void free filling of high aspect ratio vias is an extremely complex and challenging task, wherein the characteristics of the finally obtained copper metal line significantly depend on process parameters, materials and geometry of the structure of interest. Since the geometry of interconnect structures is determined by the design requirements and may, therefore, not be significantly altered for a given microstructure, it is of great importance to estimate and control the impact of materials, such as conductive and nonconductive barrier layers, of the copper microstructure and their mutual interaction on the characteristics of the interconnect structure so as to insure both high yield and the required product reliability. In particular, it is important to identify and monitor degradation and failure mechanisms in interconnect structures for various configurations so as to maintain device reliability for every new device generation or technology node.

Accordingly, a great deal of effort has been invested in investigating the degradation of copper lines, especially in view of electromigration, in order to find new materials and process strategies for forming copper metal lines. Although the exact mechanism of electromigration in copper lines is still not quite fully understood, it turns out that voids positioned in and on sidewalls and interfaces, large bulk voids and residuals at the via bottom may have a significant impact on production yield and reliability. Except for gross failures, such defects in vias, which may be provided in the form of via chains as control monitor structures in wafer scribe lines, are difficult to detect in standard electrical testing procedures.

Since advanced microstructures, such as fast microprocessors, may require an increased interconnect complexity with dense metal structures at extremely reduced dimensions, and many inspection techniques are already pushed to their limits, there exists a need for enhanced or alternative techniques to examine, monitor and control materials and process technologies involved in the fabrication of complex interconnect structures.

SUMMARY OF THE INVENTION

Generally, the present invention is directed to a technique that enables the examination of one or more characteristics of a conductive interconnect structure during the application of specified stress conditions. To this end, a portion of interest of a microstructure may be examined by using a short wavelength radiation, such as electrons and x-rays, wherein a change of at least one characteristic may efficiently be visualized and/or the examination may be performed by using an appropriately prepared sample, in which the portion of interest is maintained fully operational by providing all of the interfaces as are present in an actual device.

According to one illustrative embodiment of the present invention, a method comprises preparing a sectional sample of a portion of a conductive structure embedded in a dielectric layer of a microstructure device so as to maintain the portion embedded in the dielectric layer. Then, cross-sectional analysis measurement data from the sectional sample is obtained by electron microscopy while the portion of the conductive structure is subjected to a specified stress condition.

According to another illustrative embodiment of the present invention, a method comprises preparing a sectional sample of a portion of interest of a microstructure and generating a plurality of images of the sectional sample. Finally, the plurality of images is displayed in a quick motion mode so as to assess at least one characteristic of the portion of interest.

According to a further illustrative embodiment, a method comprises preparing a sectional sample of at least a portion of an interconnect structure positioned in a dielectric layer. The method further includes obtaining a plurality of images of at least the portion of the interconnect structure while subjecting the portion of the interconnect structure to a specific stress condition. Moreover, the plurality of images are displayed in quick motion to visualize degradation effects on the interconnect structure under the stress conditions.

According to still a further illustrative embodiment of the present invention, a sectional sample of a portion of interest of a microstructure comprises a first elongated metal region having a first longitudinal axis. The section sample further comprises a second elongated metal region having a second longitudinal axis, wherein the first and the second metal regions are connected to each other so as to form a substantially right angle with the first and second longitudinal axis. Moreover, a dielectric material encloses the first and second metal regions, wherein the dielectric material forms a layer having at least one exposed surface above the first and second metal regions, whereby a thickness of the layer is approximately 100 nm or less for imaging of degradation and failure modes using a scanning electron microscope (SEM).

BRIEF DESCRIPTION OF THE DRAWINGS

The invention may be understood by reference to the following description taken in conjunction with the accompanying drawings, in which like reference numerals identify like elements, and in which.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention will now be described with reference to the attached figures. Although the various regions and structures of a semiconductor device are depicted in the drawings as having very precise, sharp configurations and profiles, those skilled in the art recognize that, in reality, these regions and structures are not as precise as indicated in the drawings. Additionally, the relative sizes of the various features and doped regions depicted in the drawings may be exaggerated or reduced as compared to the size of those features or regions on fabricated devices. Nevertheless, the attached drawings are included to describe and explain illustrative examples of the present invention. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

It should be noted that the present invention is particularly advantageous in the context of copper-based interconnect structures, since these structures will preferably be used in advanced microstructures, such a fast microprocessors, wherein especially the problem of electromigration may significantly impact further developments in fabricating sophisticated integrated circuits. The principles of the present invention may, however, be readily applied to any microstructure of interest, in which stress-induced material transport phenomena may significantly influence the operation and the reliability of the microstructure. Consequently, stress-induced migration problems may effectively be investigated for any type of interesting conductive material, such as metals, metal alloys or metal compounds, used in present and future microstructure systems. The present invention should, therefore, not be considered as being restricted to copper-based interconnect structures unless such restrictions are explicitly set forth in the appended claims.

As is well known, the degradation of inlaid, i.e., embedded, metal lines is related to directed mass transport within the line. The gradient of the electrical potential gives migrating atoms a preferred direction to the anode. Local temperature peaks caused by increased electrical current densities lead to temperature gradients during operation of a microstructure device and, therefore, additionally thermal migration is closely connected with electromigration. It has further been proposed that mechanical stress gradients may preferably be expected for via/line structures, which, therefore, require increased efforts in investigating stress-induced material transport effects, since, additionally, in vias, the formation of barrier layers and the filling in of copper is a quite critical process sequence and may significantly contribute to the behavior of the interconnect structure. Consequently, the present invention provides for the potential of a sensitive process control or monitoring based on a large number of data to reach statistically relevant conclusions and for the study of solid state physical degradation mechanisms for representative samples so as to enhance the understanding of weaknesses in the interconnect technology and to reduce reliability-related failures in interconnect structures. To this end, fully embedded interconnect structures may be subjected to specified stress conditions while monitoring at least one characteristic of the interconnect structure. In other cases, efficient means are provided so as to effectively visualize subtle changes of a metal interconnect structure during operation.

Figure 1A:
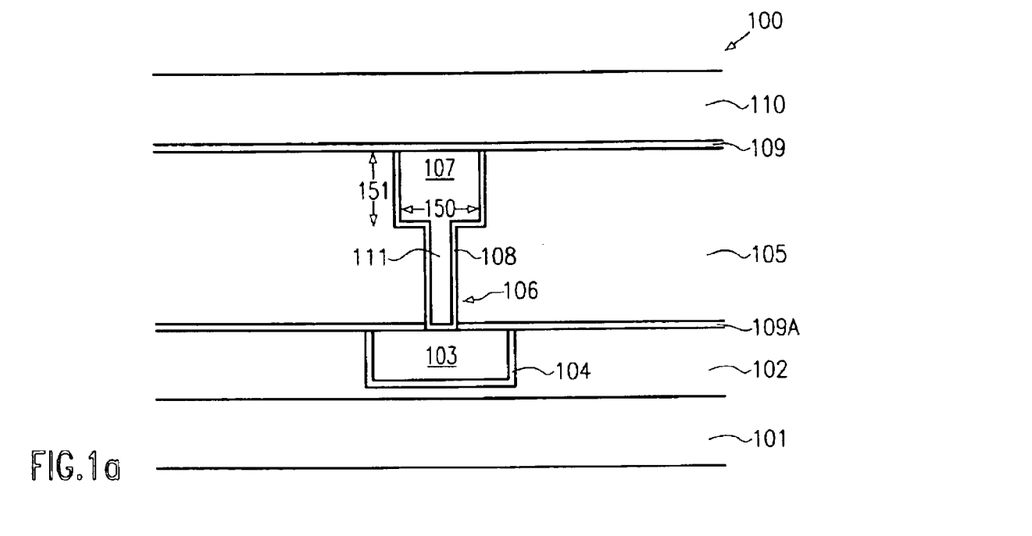
FIGS. 1A–1C schematically show a top view and two cross-sectional views, respectively, of a portion of an interconnect structure according to illustrative embodiments of the present invention.

FIG. 1A schematically shows a cross-sectional view of a sectional sample 100 representing a portion of a microstructure of interest. As previously explained, the sample 100 may represent a portion of a conductive structure on the basis of a copper metallization as may be used in advanced integrated circuits. The sample 100 comprises a substrate 101 which may be any type of appropriate substrate, such as a silicon substrate, an SOI (silicon-on-insulator) substrate, a glass substrate, or any other appropriate substrate that allows the fabrication of a microstructure including a metal interconnect structure thereon. For instance, the sample 100 may represent a portion of a substrate for producing semiconductor devices, which is actually not used for product devices. In one example, the sample 100 may be formed from a portion of a wafer scribe line.

It should be appreciated that the term "sectional" is to be understood as a section through a region of interest of a microstructure, wherein a direction of sectioning the region of interest is sufficiently aligned to a direction in which a substantial stress-induced material transportation is expected so as to enable an analysis by electron microscopy or X-ray microscopy or other visual imagery techniques. Hence, with respect to electromigration, a sectional sample is to represent a sectioned region of interest in which a certain length of a metal line along the direction of the current may be observed.

The substrate 101 may have formed thereon one or more material layers and/or microstructure elements (not shown) as are fabricated during preceding manufacturing processes. A first dielectric layer 102 is formed above the substrate 101 and may be comprised of any appropriate dielectric material, such as silicon dioxide, silicon nitride, or any low-k dielectric materials, such as SiCOH, hydrogenated silicon carbide or other polymeric low-k materials. A metal line 103 is formed in the first dielectric layer 102, wherein the metal line 103 may be substantially comprised of copper or any other appropriate metal. Moreover, the metal line 103 may comprise a conductive barrier layer 104, especially if the metal line 103 is a copper-based metal line, wherein the barrier layer 104 may be a single layer or may be composed of a plurality of sub-layers that are formed and selected in accordance with process and device requirements. For instance, currently tantalum and tantalum nitride are preferred materials for the barrier layer 104 in copper-based metallization structures. It should be noted, however, that any other presently known material or material composition or any future material compositions may be selected for the barrier layer 104, wherein the present invention provides the potential for assessing these materials in combination with their manufacturing processes in view of their impact on stress-induced material transportation in metal lines. The sample 100 further comprises a second dielectric layer 105 that may be comprised of substantially the same materials as are referred to in context with the first dielectric layer 102. A conductive structure 106, for instance in the form of an interconnect structure, comprised of a metal line 107 and a metal-filled via 111, is formed in the second dielectric layer 105, wherein the conductive structure 106 may comprise a barrier layer 108 that is in contact with the second dielectric layer 105. Regarding the material composition of the barrier layer 108, substantially the same criteria apply here as previously explained with reference to the barrier layer 104.

In one particular embodiment, at least the conductive structure 106 has a geometrical configuration, i.e., dimensions and an arrangement, which substantially corresponds to a specified microstructure design under consideration. For instance, the metal line 107 and the via 111 may include copper, wherein a width of the metal line 107, i.e., in FIG. 1A, the horizontal extension of the metal line 107 (in the direction indicated by the double arrow 150), may range from 0.1 $\mu$m or even less to 1 $\mu$m or more, whereas a depth, i.e., in FIG. 1A, the vertical extension of the metal line 107 (in the direction indicated by the double arrow 151), may range from approximately 0.1 $\mu$m to 0.5 $\mu$m or more. The via 111 may have a depth of several hundred nanometers, with a lateral dimension, i.e., a diameter if a circular geometry is considered, of several hundred nanometers to even less than 100 nanometers in advanced microprocessors. It should be noted that the first metal line 103 may represent a metal line having a configuration and dimensions in accordance with the specified microstructure design, whereas, in other embodiments, the metal line 103 may be configured such as to allow the operation of the conductive structure 106 at an elevated current density while substantially not affecting the current supply to the interconnect structure 106.

Furthermore, the sample 100 comprises a dielectric capping layer 109 comprised of a material that provides the necessary adhesion and that enables an efficient suppression of diffusion of metal from the metal line 107 into adjacent material regions. For instance, the capping layer 109 may be comprised of silicon nitride, nitrogen-rich silicon carbide and the like. Above the capping layer 109, a third dielectric layer 110 may be formed that is comprised of any material as previously described with reference to the dielectric layers 102 and 105.

A typical process flow for forming the sample 100 as shown in FIG. 1A may comprise the following processes. First, the metal line 103, including the barrier layer 104, may be formed in the first dielectric layer 102 in accordance with process techniques that will be described in more detail with reference to the conductive structure 106. After completion of the metal line 103, a capping layer 109A, which also acts as an etch stop layer during the formation of the conductive structure 106, is deposited, for instance, in the form of a silicon nitride layer. Thereafter, the second dielectric layer 105 may be deposited by any appropriate deposition method, such as chemical vapor deposition, from suitable precursor gases, such as TEOS or silane when the second dielectric layer 105 is substantially comprised of silicon dioxide. In other cases, the second dielectric layer 105 may be formed by spin-on techniques, when the second dielectric layer 105 represents a low-k polymer material. Next, the second dielectric layer 105 is patterned by sophisticated photolithography and etch techniques, wherein according to one approach of the damascene technique, the via 111 may be etched through the entire dielectric layer 105, wherein the etch process is stopped in the capping layer 109A.

Thereafter, a further photolithography process and a further etch process may be performed to etch a trench for the metal line 107 in the upper portion of the dielectric layer 105. Thereafter, the via 111 may be completely opened so as to provide a connection to the underlying metal line 103, and the barrier layer 108 may be deposited by, for instance, chemical vapor deposition, physical vapor deposition, such as sputter deposition, atomic layer deposition techniques, and the like. Depending on the geometry of the conductive structure, 106, i.e., depending on the dimensions, and depending on the type of materials used, a corresponding deposition technique in combination with appropriate process parameters may be used. For instance, a tantalum/tantalum nitride layer may be formed by sputter deposition so as to provide the barrier layer 108, wherein the process parameters, such as pressure, bias voltage and the like within the sputter atmosphere, are selected so as to reliably cover the entire inner surfaces of the interconnect structure 106 with a required minimum thickness of the barrier material. Since the reliable coverage of high aspect ratio openings, such as the via 111, with a thin material layer is a quite complex process, precise control and monitoring of the deposition process is required, especially, as previously pointed out, as the characteristics of an interface between the barrier layer 108 within the via 111 and the metal line 107 and the interface to the surrounding dielectric may significantly influence the behavior of the conductive structure 106 during operation.

After formation of the barrier layer 108, depending on the type of metal to be filled-in in the interconnect structure 106, a seed layer may be deposited so as to promote the metal deposition during a subsequent plating process. A corresponding seed layer be deposited by chemical or physical vapor deposition, by electroless plating and the like. Thereafter, metal is filled in the via 111 and the trench so as to form the interconnect structure 106 including the metal line 107 and the metal filled via 111. A currently preferred deposition technique for copper is electroplating, wherein the composition of the plating solution, the waveforms of the current supplied to the plating reactor and the like are controlled to obtain a deposition process that substantially fills the interconnect structure 106 from bottom to top. Thereafter, in some process schemes, an anneal process may be performed to correspondingly adjust the crystallinity of the copper. As a next step, excess metal is removed, for instance, by chemical mechanical polishing (CMP) and/or electropolishing, thereby also planarizing the surface of the second dielectric layer 105. In some process flows, an anneal process may be performed after the CMP process. Since the upper surface of the metal line 107 is exposed during and after the planarizing process, which may lead to corrosion and discoloration on the surface, a cleaning process is performed followed by a deposition process to form the capping layer 109. As previously explained, stress-induced material transport, such as electromigration, may preferably take place at interfaces in the interconnect structure 106. Accordingly, the selected material and the deposition parameters for forming the capping layer 109 may significantly influence the performance of the interconnect structure 106 during operation. Finally, the dielectric layer 110 is deposited by any appropriate technique, depending on the type of material used for the dielectric layer 110.

It should be noted that the above-described process for forming the interconnect structure is illustrative and depends on the overall process strategies. The following processes and actions of the present invention apply to any process technique, irrespective of the process flow that is actually used.

As is evident from the above description, a plurality of processes and materials are involved in forming the interconnect structure 106, at least some of which may significantly affect the characteristics, such as the microstructure of the metal, the formation of internal interfaces in the form of voids, the type and quality of interfaces between the metal and the barrier layer 108, as well as the interface and quality between the metal and the capping layer 109.

Figure 1B:
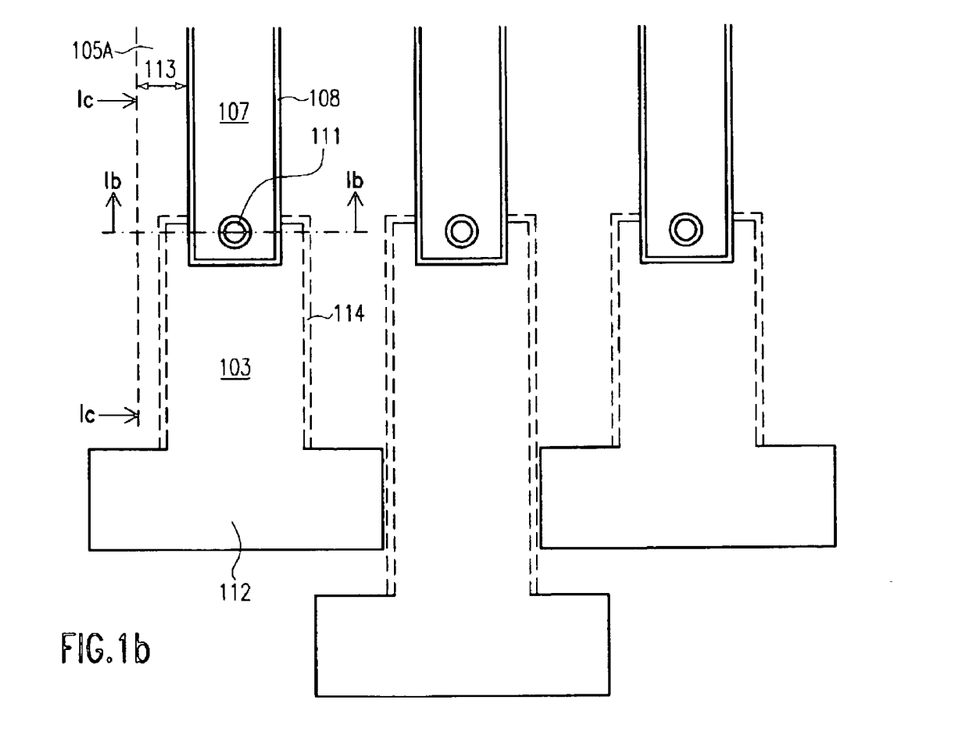

FIG. 1B schematically shows a top view of a portion of the sample 100. For convenience, the dielectric layer 110, the capping layer 109, the dielectric layer 105, the capping layer 109A and the dielectric layer 102 are shown as being transparent, wherein the metal line 103, underlying the conductive structure 106, is shown in dashed lines. As shown in FIG. 1B, the metal line 103 is connected to a contact pad, which is schematically represented by 112 and should merely indicate that the metal line 103 may be connected to an external current source. Similarly, the metal line 107 is configured such that it can be connected to the external current source, wherein the connection may be provided in the form of a further interconnect structure, such as the structure 106, connected to a corresponding lower lying metal line (not shown) that may have the same structure as the metal line 103. In other embodiments, the metal line 107 may be connected to a contact pad or to another metal line within the same metallization layer. Moreover, a plurality of interconnect structures 106 may be provided so as to facilitate the preparation of the sample 100 in a subsequent sample preparation process using an FIB (focused ion beam) tool.

As previously explained, it is important for present and future device generations to investigate the degradation mechanisms of interconnect structures, since these degradations may represent a major source of device failures in advanced microstructures operated at high current densities. Since any interfaces between the metal and adjacent materials have been identified as material transportation paths, the sample 100 is prepared according to the present invention such that all interfaces of the interconnect structure 106 remain intact while, nevertheless, providing the possibility for monitoring the state of the conductive structure 106 during operation usually by, for example, means of short wavelength radiation, such as an electron beam or an x-ray beam. To this end, the substrate 101 is cut such that at least some of the interconnect structures 106 (see FIG. 1B) are in the vicinity of the cut line and the final sample preparation is performed by a focused ion beam process in such a way that a section is carried out along a line, as indicated as Ic in FIG. 1B. In sectioning the substrate 101 by the focused ion beam, the beam is positioned such that the interconnect structure 106 remains fully embedded in the dielectric layer 105 so as to maintain the interface of the barrier layer 108 with the surrounding dielectric of the layer 105, since the conductive barrier layer 108 also contributes to the current transportation within the interconnect structure 106. The remaining layer of dielectric material "in front" of the interconnect structure 106 is denoted by 105A.

For the subsequent studies using scanning electron microscopy (SEM), in some embodiments, the focused ion beam is positioned such that a thickness 113 of the dielectric layer 105 that is preserved is 100 nm and less. In other embodiments, the thickness 113 is in the range of approximately 50–100 nm, whereas, in other embodiments, a thickness of less than 50 nm may be obtained, depending on the positional accuracy obtainable with the FIB tool used. In the embodiment shown in FIG. 1B, the metal line 107 and the underlying metal line 103 may have a significant overlap at the side of the section Ic, depending on the design of the sample 100. When the metal line 103 is merely considered as a supply line for the interconnect structure 106, the section Ic may cut through the metal line 103 substantially without affecting the subsequent monitoring of the degradation process of the interconnect structure 106. Hence, the thickness 113 may be adjusted to the above-identified range irrespective of the degree of alignment of the edges of the metal lines 107 and 103 at the side of the section Ic. In other cases, as shown in FIG. 1B, the line 103 may also remain embedded in the dielectric layer 105.

In one illustrative embodiment, the sectional sample 100 is intended to be used for surface and interface sensitive measurements by electron microscopy and, therefore, the section Ic provides a surface for the incoming electron beam, wherein the reduced thickness 113 of the preserved dielectric material of the layer 105, i.e., the layer 105A, insures that the incoming electrons pass through the remaining dielectric material even at moderate electron energies. In a further illustrative embodiment, the sectional sample 100 is prepared in such a way that volume sensitive measurement data may be obtained by x-ray microscopy. To this end, the sectional sample 100 may be prepared as a lamella with a thickness of approximately 1–2 μm, depending on the primary energy of the radiation, in that the sample 100 as shown in FIG. 1B is additionally cut along the section 114 by a focused ion beam.

Figure 1C:
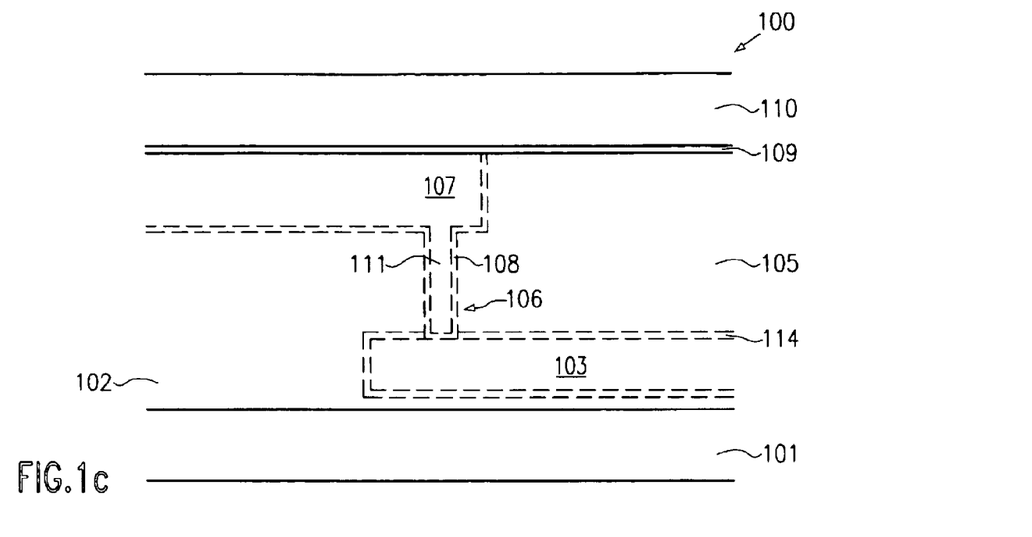

FIG. 1C schematically shows the sectional sample 100 when viewed perpendicularly to the surface provided by the remaining dielectric layer 105A (see FIG. 1B), wherein it is assumed that the dielectric layer 105A in front of the interconnect structure 106 is transparent. Consequently, the sectional sample 100 enables the investigation of degradation mechanisms of the interconnect structure 106 during operation under substantially "real" conditions, since the interconnect structure 106 is fully embedded in the dielectric material as is used in the microstructure of interest. It should be noted that the interconnect structure 106 is of illustrative nature only, and any other interconnect structure of interest may be formed and provided as a sectional sample in the above-described fashion. For instance, if the degradation mechanism in a single metal line of specified configuration has to be investigated, a corresponding line portion may be manufactured, wherein corresponding current supply lines may then be connected to the metal line portion. In the same manner, a plurality of stacked interconnect structures may be formed in accordance with a microstructure design of interest, thereby providing the potential for observing the characteristics of such interconnect structures on a more "global" scale.

Figure 2:
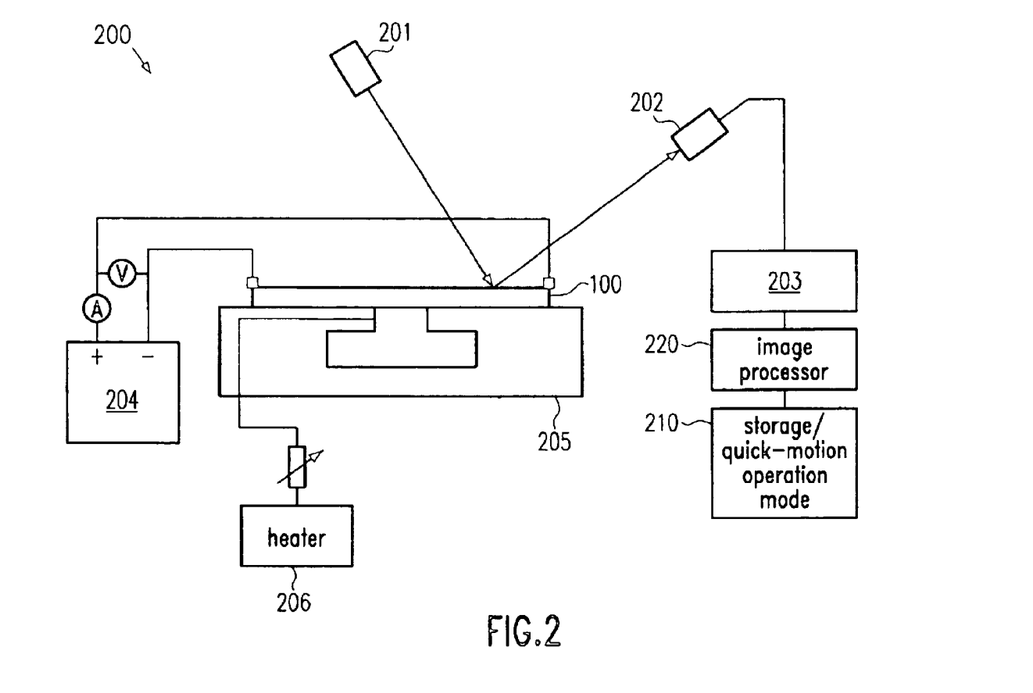
FIG. 2 schematically illustrates a measurement system for evaluating characteristics of a fully embedded interconnect structure as shown in FIGS. 1A–1C.

With reference to FIG. 2, further illustrative embodiments of the present invention regarding the monitoring and investigation of characteristics of the interconnect structure 106 will now be described in more detail. In FIG. 2, a system 200 comprises a source of short-wavelength radiation 201 and a detector 202 that is configured to detect secondary radiation generated by the incoming short-wavelength radiation and to provide cross-sectional measurement data in the form of corresponding signals to a signal processing unit 203. The system 200 further comprises a sample holder 205 that is configured to receive and hold in position an appropriate sectional sample, such as the sample 100 as described with reference to FIGS. 1A–1C. As previously noted, surface and interface sensitive measurements may be performed by means of an electron beam so that the electron source 201, the detector 202 and the signal processing unit 203 may be provided in the form of a scanning electron microscope. For instance, an LEO Gemini 1550 electron microscope may be used for this purpose. In other embodiments, the detector 202 may be configured so as to enable the detection of radiation passing through the sample 100. For instance, the radiation source 201, the detector 202 and the signal processing unit 203 may represent a transmission x-ray microscope, which enables the detection of material transport within the entire interconnect structure 106. Appropriate x-ray microscopes are well known in the art. However, as will be recognized by those skilled in the art after a complete reading of the present application, the present invention may be employed with a variety of different systems and techniques that enable the interconnect structure 106 to be visually observed to detect or investigate degradation of the interconnect structure due to, for example, electromigration, as described more fully below. Thus, the present invention should not be considered as limited to any particular system or technique unless such limitations are expressly set forth in the appended claims. Typically, the system comprises a process chamber and any means for establishing required pressure conditions therein, which are, for convenience, not shown.

The system 200 further comprises an adjustable current source 204 that may be connected to the interconnect structure via, for instance, the contact pads 112 (see FIG. 1B) and corresponding wires bonded to the contact pads and to a test package which, in turn, may be inserted into an appropriate test socket. In one particular embodiment, the system 200 comprises a heater 206 that is configured to adjustably heat the sample 100 via the sample holder 205.

Depending on the capabilities of the process chamber accommodating the sample holder 205, the system 200 may comprise further means so as to adjust the environmental conditions of the sample 100. For instance, the atmospheric pressure surrounding the sample 100 may be adjustable by means of a corresponding pump source and/or mechanical stress may be externally applied to the sample 100, for instance, by locally exerting a force to the sample 100 and/or the humidity of the atmosphere may be controlled, and the like.

The system 200 further comprises a memory unit 210 that is configured to receive corresponding signals from the signal processing unit 203, for instance, in the form of images, e.g., two-dimensional images, of a region of interest in the sample 100. In one particular embodiment, the memory unit 210 may comprise a processor section that is configured to provide at least some of the two-dimensional images stored in a quick motion representation. In some embodiments, the system 200 may comprise an image processor 220 that is configured to receive the processed signals from the signal processing unit 203 and perform a data manipulation on these signals, such as contrast enhancement, selection of a region of interest and the like, prior to supplying the images to the memory unit 210.

During the operation of the system 200, the sample 100 may be mounted on the sample holder 205 and a specified stress condition may be applied to the sample 100. Since the investigation of electromigration is of great interest for the development of interconnect structures of highly complex integrated circuits, preferably the stress condition includes the application of a specified current by means of the adjustable current source 204 so as to create a specified initial current density in the interconnect structure 106. Moreover, the sample 200 may be heated to a specified temperature, or portions of the sample 100 may be heated to a specified temperature so as to create a temperature gradient within the sample 100. For example, in one illustrative embodiment, the applied current density may be on the order of approximately 20 MA/cm$^2$ (Mega Ampere per square centimeter), and the sample 200 may be heated to a temperature on the order of approximately 250° C. As previously pointed out, depending on the capabilities of the system 200 in establishing specified environmental conditions for the sample 200, additionally or alternatively other stress conditions may be established, such as mechanical stress, atmospheric pressure and the like. For instance, the degradation of the interconnect structure 106 may be examined under sophisticated environmental conditions even if the interconnect structure 106 is not operated or is merely temporarily operated so as to estimate the influence of environmental conditions on the overall reliability and performance of the interconnect structure 106. Of course, the stress condition created may be varied over time or the magnitude of the stress condition may be varied if desired.

During the application of a specified stress condition to the sample 100, the short wavelength radiation is directed to the sample 100, either continuously or intermittently at predefined time intervals, and the corresponding primary or secondary radiation is received by the detector 202. For instance, when the radiation source 201, the detector 202 and the signal processing unit 203 are provided in the form of an x-ray microscope, the sample 100 may be provided in the form of a lamella, the transmitted or scattered x-rays may be detected and processed so as to create corresponding images of the interconnect structure 106, which provide visibility of material transport substantially through the entire interconnect structure. Thereafter, the images provided from the signal processing unit 203 may further be manipulated by the image processor 220 and are then stored in the memory unit 210. Finally, at least some of the plurality of images stored in the memory unit 210 may be compiled in a form that is appropriate to be displayed in a quick motion mode. To this end, the memory unit 210 may be implemented in a personal computer, or any other appropriate means that allows the storage of the plurality of images and also provides the possibility for appropriately displaying the plurality of images in the form of a "movie." It should be noted that the image processor 220, if provided, may also be implemented in the personal computer so that any desired image manipulation may be performed to appropriately adapt the quick motion representation in conformity with a characteristic of interest. That is, subtle portions within an image possibly including any shadings or other features may be selected and may be manipulated so as to enhance or attenuate these features. The corresponding image processing may then be automatically applied to the remaining images, thereby providing the possibility to visualize a change in the images in the form of a movie under different criteria. The quick motion or movie representation of the measurement results obtained by the system 200 provides for the potential of effectively identifying a change in one or more characteristics of the interconnect structure 106 by visual observation of the movie.

FIGS. 3A–3D schematically represent images obtained by scanning electron microscopy at various stages of test runs, when an interconnect structure, such as the structure 106, was subjected to a stress condition, including heating to approximately 150° C. and applying a current density of approximately 30 MA/cm$^2$ within the via 111.

Figure 3A:
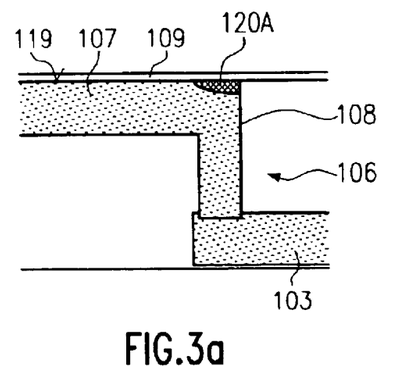
FIGS. 3A–3D schematically illustrate a typical measurement result in the form of cross-sectional images of a interconnect structure at different times during the application of a specified stress condition.

FIG. 3A represents a visual image of the structure 106 after the structure 106 was subjected to the stress condition for several hours. As described therein, a migration process, as indicated by the number 120A, is occurring at the interface 119 between the metal in the line 107, i.e., the copper, and the capping layer 109, which in the present example is comprised of silicon nitride. The intensity of the migration process 120A depends on the current density and the temperature as well as on the duration of the stress conditions.

Figure 3B:
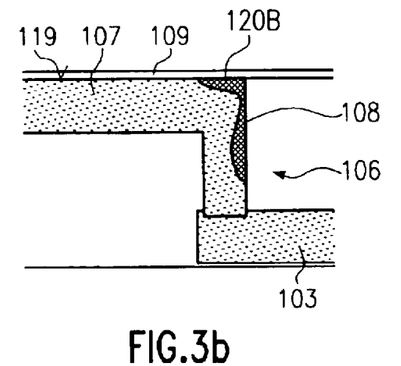

FIG. 3B is a visual image of the structure 106 after several hours of applied stress condition similar to that in FIG. 3a. As depicted, the migration of copper is occurring along the capping layer 109 and along the inner surface of the void represented at 120B, created by the material transport.

Figure 3C:
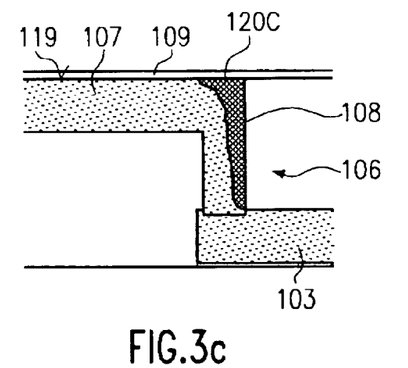

FIG. 3C is a visual image of the structure 106, wherein the stress condition applied for several hours results in grain boundary diffusion and void agglomeration in the via 111, as indicated by the number 120C.

Figure 3D:
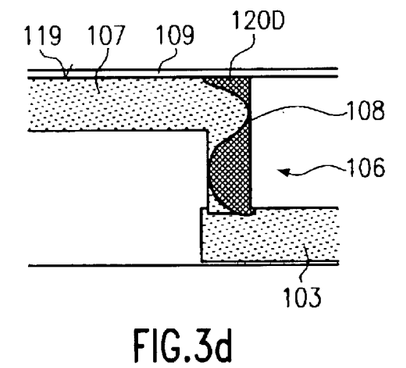

FIG. 3D is a visual image of the structure 106 after applying the stress condition for several hours resulting in the growth of the void, indicated by the number 120D, that seems mainly caused by atomic transport along inner surfaces, thereby leading to a copper redeposition.

As previously explained, a plurality of images may be obtained, which may be displayed in a quick motion mode so as to more clearly visualize even subtle changes within the interconnect structure 106. For instance, a corresponding movie may be made including the images representing a measurement period of a few hours to a few days. Depending on the selected short wavelength radiation, i.e., electrons in an energy range of approximately 10–30 keV or x-rays, interface sensitive or volume sensitive measurements may be obtained.

Due to the display of the measurement results in the form of a "movie"-like representation, even subtle variations of measurement results of different interconnect structures may efficiently be identified. Hence, the various contributions of materials and/or process parameters of the manufacturing sequence on the degradation process may be compared so as to obtain a correlation between one or more materials, process parameters and stress conditions applied to the test samples.

Figure 4:
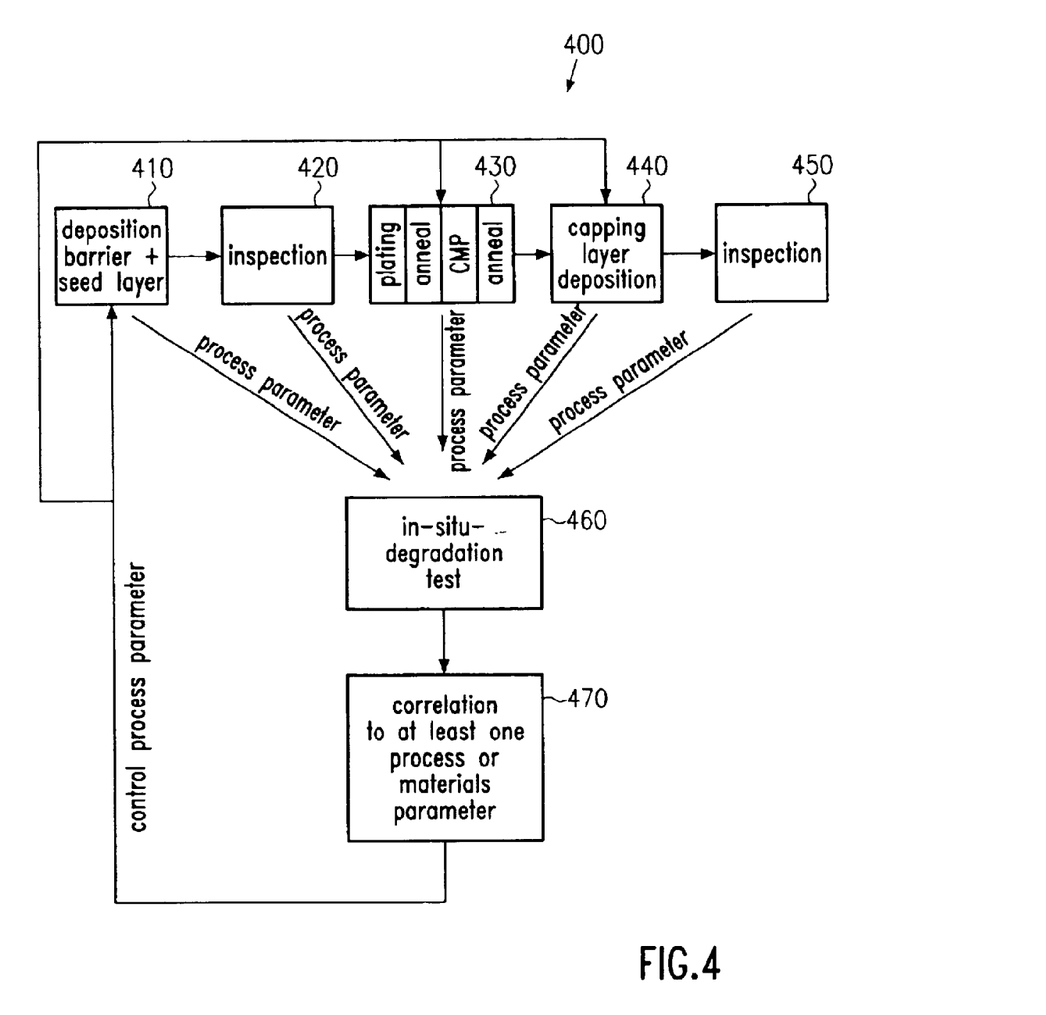
FIG. 4 schematically depicts a process sequence for manufacturing an interconnect structure on the basis of an in situ degradation test in accordance with further illustrative embodiments of the present invention.

FIG. 4 schematically represents a process sequence 400 for forming a metal line or an interconnect structure as is, for example, described with reference to FIGS. 1A–1C. Box 410 represents processes related to the formation of a barrier layer and possibly of a seed layer, wherein these processes may include chemical and physical vapor deposition, atomic layer deposition, electroless plating processes and the like. Box 420 represents any inspection processes performed after having formed the barrier layer. Box 430 represents the plating process, such as an electroplating process, for depositing large amounts of copper as is previously described. Moreover, box 430 represents any post-plating processes, such as CMP, electropolishing and the like, for removing excess material as well as any anneal cycles performed prior to and/or after a CMP process. A next step of the process sequence 400 is represented by box 440 indicating the deposition of a capping layer, such as the capping layer 109. Thereafter, box 450 may represent any inspection and measurement procedures after completion of the interconnect structure under consideration. In the process steps 410 . . . 450 materials and process parameters may change in accordance with device and process requirements for the microstructure of interest as, for example, the barrier and adhesion function is essential for the proper operation of the interconnect structure and may even gain in importance as feature sizes are decreased. As previously explained, a complex mutual interaction of the materials and process parameters may significantly influence the finally obtained degradation behavior of the interconnect structure of interest. Therefore, according to one illustrative embodiment, an in situ degradation test, represented by box 460, may be performed similar to that described with reference to FIG. 2, thereby allowing a sensitive monitoring of the involved materials and process parameters. For instance, a change of the geometry, i.e., the dimensions of the vias and/or the metal lines, may lead to subtle changes of the characteristics of the finally obtained interconnect structure, although substantially the same process parameters and materials may have been used in the manufacturing sequence 410 . . . 450, as in a previously fabricated interconnect structure that exhibits satisfactory results. Based on the in situ degradation test 460, one or more materials or process parameters may then be identified as the root cause of the observed degradation by correspondingly varying one or more process parameters and materials for a plurality of test samples.

Moreover, the in situ degradation test 460 enables efficient monitoring or process variations within the sequence 410 . . . 450, which may not have been identified within the individual processes. For instance, according to the results provided by the inspection processes 420 and 450 and additional metrology processes, the individual processes 410, 430, 440 may lie within the individually defined process margins, while, nevertheless, the finally obtained interconnect structure may fail in the degradation test. In other embodiments, a correlation may be established, as indicated by 470, that relates at least one process parameter and/or material to the measurement results obtained in the degradation test 460, so that a "long term" process control may be achieved. For instance, from previously performed reference measurements, the influence of, for example, process materials and parameters of the barrier/seed deposition process 410 may have been determined for a plurality of materials and process parameter values. Upon detection of a deviation of periodically performed degradation tests 460, a corresponding readjustment of process parameters and/or materials may then be performed. Thereafter, process operations may be performed on one or more subsequently processed substrates using the adjusted parameters and/or adjusted materials. The same holds true for the further process steps 420 . . . 450. For instance, measurement results of the inspection steps 420 and 450 may effectively be correlated to the results of the in situ degradation test 460, thereby providing the capability for detecting relevant process fluctuations at an early stage in the process sequence 410 . . . 450. For example, measurement results with respect to texture, grain size, mechanical stress of the inlaid copper after the plating process 430, may be related to degradation mechanisms identified in the degradation test 460, wherein by means of the correlation 470 and corresponding routinely performed measurements, a process fluctuation may be identified, which may have otherwise been estimated as negligible. In this way, the "sensitivity" of one or more inspection processes involved in the sequence 410 . . . 450 may be enhanced with respect to the finally obtained reliability of interconnect structures. Moreover, the effective visualization of subtle changes in the interconnect structure in the form of a quick motion mode provides the possibility for efficiently investigating various influences on the degradation mechanisms of interconnect structures under a wide range of stress conditions.

As a result, the present invention provides a technique for visually investigating the degradation of conductive structures, such as metal lines and metal interconnect structures, especially of copper-based interconnect structures, in that fully embedded metal line portions are examined under various stress conditions by scanning electron microscopy, wherein, in some embodiments, test results are also obtained by x-ray scattering and are visualized in a highly efficient manner by displaying a plurality of images in a quick motion mode, thereby enabling the detection of even subtle changes in at least one characteristic of the interconnect structure.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method, comprising:
   preparing a sectional sample of a portion of a conductive structure embedded in a dielectric layer of a microstructure device so as to maintain said portion embedded in said dielectric layer; and
   obtaining cross-section analysis measurement data of said sectional sample by electron microscopy while subjecting said portion of said conductive structure to a specified stress condition.

2. The method of claim 1, wherein said conductive structure is comprised of a metal.

3. The method of claim 1, wherein said conductive structure is comprised of copper.

4. The method of claim 1, wherein said cross-section analysis measurement data are obtained in the form of at least one image.

5. The method of claim 1, wherein said conductive structure is formed in accordance with a predefined manufacturing sequence for said microstructure device.

6. The method of claim 5, further comprising assessing said predefined manufacturing sequence on the basis of said at least one image.

7. The method of claim 5, further comprising obtaining a correlation between at least one process parameter of said predefined manufacturing sequence and said cross-section analysis measurement data.

8. The method of claim 7, further comprising:
preparing a second sectional sample of a portion of a conductive structure embedded in a dielectric of a microstructure device so as to maintain said portion embedded in said dielectric;
obtaining second cross-section analysis measurement data from said second sectional sample while subjecting said portion of said conductive structure to a specified stress condition; and
controlling said at least one process parameter on the basis of said correlation and said second cross-section analysis measurement data.

9. The method of claim 1, wherein said specified stress condition comprises generating a predefined initial current density in said metal line.

10. The method of claim 1, wherein said specified stress condition comprises heating said sectional sample.

11. The method of claim of claim 1, further comprising obtaining a plurality of images of said sectional sample and displaying said plurality of images in quick motion to visualize degradation effects of said conductive structure under said specified stress condition.

12. The method of claim 1, wherein preparing said sectional sample comprises forming a first metal line, a second metal line and an interconnect in said microstructure device, said interconnect connecting said first and second metal lines, and cutting said microstructure device and thinning a cut portion thereof to obtain said sample, wherein said sample includes said interconnect embedded in a dielectric.

13. The method of claim 12, wherein forming said first and second metal lines and said interconnect includes forming said first metal line in a first metallization layer and forming said second metal line and said interconnect commonly in a second metallization layer.

14. The method of claim 13, wherein said first and second metal lines and said interconnect comprise copper and a conductive barrier layer separating at least some of the sidewalls of said first and second metal lines and said interconnect from adjacent dielectric material.

15. The method of claim 14, wherein said conductive structure comprises a dielectric barrier layer forming an interface with copper.

16. The method of claim 1, wherein a thickness of dielectric material forming a surface over said first and second metal lines and said interconnect and being exposed to short wavelength radiation during obtaining said cross-section analysis measurement data is approximately 100 nanometer or less.

17. The method of claim 16, wherein an energy of said short wavelength radiation is selected so as to at least transmit through said thickness of said dielectric material.

18. The method of claim 1, wherein said conductive structure has a plurality of side surfaces and a plurality of end surfaces, wherein said dielectric layer encapsulates said side surfaces of said conductive structure.

19. The method of claim 1, wherein said sectional sample comprises:
a first elongated metal region having a first longitudinal axis;
a second elongated metal region having a second longitudinal axis, the first and second metal regions connected to each other so as to form a substantially right angle with first and second longitudinal axis; and
a dielectric material enclosing said first and second metal regions, said dielectric material forming a layer having at least one exposed surface above said first and second metal regions, wherein a thickness of said layer is approximately 100 nanometer or less for scanning electron microscopy studies.

20. A method, comprising:
preparing a sectional sample of a portion of interest of a microstructure, wherein said portion of interest comprises at least one conductive structure embedded in a dielectric material;
generating a plurality of images of said sectional sample; and
displaying said plurality of images in a quick motion mode so as to assess at least one characteristic of said portion of interest.

21. The method of claim 20, wherein said plurality of images are generated by exposing said sectional sample to short wavelength radiation.

22. The method of claim 21, wherein said short wavelength radiation is comprised of an electron beam.

23. The method of claim 20, further comprising applying a specified stress condition to said sectional sample prior to generating at least some of said plurality of images.

24. The method of claim 23, wherein applying a specified stress condition includes flowing a current through said conductive structure.

25. The method of claim 23, wherein applying a specified stress condition includes heating said sectional sample.

26. The method of claim 25, wherein said conductive structure comprises a conductive barrier layer forming an interface with metal in said metal layer and with a dielectric in which said conductive structure is embedded.

27. The method of claim 26, wherein said at least one characteristic includes material transport along said interfaces.

28. The method of claim 25, wherein said metal line comprises copper.

29. The method of claim 20, wherein said at least one characteristic includes stress-induced material transport in said conductive structure.

30. The method of claim 20, wherein said at least one characteristic includes at least one of grain size, texture and stress components in at least one specified direction.

31. The method of claim 20, further comprising obtaining a correlation between said at least one characteristic and at least one process parameter for manufacturing said microstructure.

32. The method of claim 31, further comprising controlling said at least one process parameter during the fabrication of at least one further microstructure including said portion of interest on the basis of said correlation.

33. The method of claim 20, wherein said portion of interest includes at least one metal line and wherein said sample is prepared so as to maintain said at least one metal line embedded in said dielectric.

34. The method of claim 33, wherein preparing said sectional sample includes maintaining at least one surface of said dielectric that is exposed to the short wavelength radiation with a thickness of 100 nanometer or less.

35. A method, comprising:
preparing a sectional sample of at least a portion of an interconnect structure positioned in a dielectric layer;
obtaining a plurality of images of at least said portion of said interconnect structure while subjecting said portion of said interconnect structure to a specific stress condition; and
displaying said plurality of images in quick motion to visualize degradation effects on said interconnect structure under said stress conditions.

36. The method of claim 35, wherein said interconnect structure is a metal line.

37. The method of claim 35, wherein said interconnect structure is comprised of copper.

38. The method of claim 35, wherein said plurality of images is obtained by at least one of scanning electron microscopy and x-ray microscopy.

39. A sectional sample of a portion of interest of a microstructure, comprising:
a first elongated metal region having a first longitudinal axis;
a second elongated metal region having a second longitudinal axis, the first and second metal regions connected to each other so as to form a substantially right angle with first and second longitudinal axis; and
a dielectric material enclosing said first and second metal regions, said dielectric material forming a layer having at least one exposed surface above said first and second metal regions, wherein a thickness of said layer is approximately 100 nanometer or less for scanning electron microscopy studies.

40. The sectional sample of claim 39, wherein said first and second metal regions comprise a conductive barrier layer in contact with said dielectric material.

41. The sectional sample of claim 39, wherein said first and second metal regions comprise copper.

42. The sectional sample of claim 39, wherein at least one of said first and second metal regions comprises a dielectric capping layer in contact with said copper.

43. A method, comprising:
preparing a sectional sample of a portion of interest of a microstructure, wherein said portion of interest comprises at least one conductive structure embedded in a dielectric material, said microstructure comprising:
a first elongated metal region having a first longitudinal axis,
a second elongated metal region having a second longitudinal axis, the first and second metal regions connected to each other so as to form a substantially right angle with first and second longitudinal axis, and
a dielectric material enclosing said first and second metal regions, said dielectric material forming a layer having at least one exposed surface above said first and second metal regions, wherein a thickness of said layer is approximately 100 nanometer or less for scanning electron microscopy studies;
generating a plurality of images of said sectional sample; and
displaying said plurality of images in a quick motion mode so as to assess at least one characteristic of said portion of interest.

44. The method of claim of claim 43, further comprising obtaining a plurality of images of said sectional sample and displaying said plurality of images in quick motion to visualize degradation effects of said conductive structure under said specified stress condition.

45. A method, comprising:
preparing a sectional sample of at least a portion of an interconnect structure positioned in a dielectric layer, said interconnect structure comprising:
a first elongated metal region having a first longitudinal axis,
a second elongated metal region having a second longitudinal axis, the first and second metal regions connected to each other so as to form a substantially right angle with first and second longitudinal axis, and
a dielectric material enclosing said first and second metal regions, said dielectric material forming a layer having at least one exposed surface above said first and second metal regions, wherein a thickness of said layer is approximately 100 nanometer or less for scanning electron microscopy studies;
obtaining a plurality of images of at least said portion of said interconnect structure while subjecting said portion of said interconnect structure to a specific stress condition; and
displaying said plurality of images in quick motion to visualize degradation effects on said interconnect structure under said stress conditions.

46. The method of claim 45, wherein said at least one characteristic includes stress-induced material transport in said conductive structure.

47. The method of claim 45, wherein said at least one characteristic includes at least one of grain size, texture and stress components in at least one specified direction.

* * * * *